(12) United States Patent
Koenig (10) Patent No.: US 7,689,544 B2
(45) Date of Patent: Mar. 30, 2010

(54) AUTOMATIC INDEXING OF DIGITAL IMAGE ARCHIVES FOR CONTENT-BASED, CONTEXT-SENSITIVE SEARCHING

(75) Inventor: Helmut Koenig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 662 days.

(21) Appl. No.: 10/897,102

(22) Filed: Jul. 23, 2004

(65) Prior Publication Data
US 2005/0021512 A1 Jan. 27, 2005

(30) Foreign Application Priority Data
Jul. 23, 2003 (DE) .............................. 103 33 530

(51) Int. Cl.
*G06F 17/30* (2006.01)
(52) U.S. Cl. .................. 707/3; 707/104.1; 707/10; 353/25; 705/2
(58) Field of Classification Search .............. 707/3, 707/1, 104.1, 10; 382/170; 345/854; 353/25; 705/2, 3
See application file for complete search history.

(56) References Cited

U.S. PATENT DOCUMENTS

| | | | | | |
|---|---|---|---|---|---|
| 5,517,405 | A | * | 5/1996 | McAndrew et al. | 706/45 |
| 5,842,009 | A | * | 11/1998 | Borovoy et al. | 707/1 |
| 6,522,780 | B1 | * | 2/2003 | Pass et al. | 382/170 |
| 7,043,472 | B2 | * | 5/2006 | Aridor et al. | 707/3 |
| 2002/0097278 | A1 | * | 7/2002 | Mandler et al. | 345/854 |
| 2003/0187592 | A1 | * | 10/2003 | Ohta et al. | 702/20 |
| 2004/0047357 | A1 | | 3/2004 | Rabaioli | |

FOREIGN PATENT DOCUMENTS

DE 100 48 479 A1 4/2002

OTHER PUBLICATIONS

C. Faloutsos, D.Oard: "A survey of information retrieval and filtering methods", Technical report, Information, filtering project, University of Maryland, College Park, MD, 1996, S. 1-23.

(Continued)

*Primary Examiner*—Hosain T Alam
*Assistant Examiner*—Jieying Tang
(74) *Attorney, Agent, or Firm*—Harness, Dickey & Pierce, P.L.C.

(57) ABSTRACT

A method is for automatically indexing multimedia data archives and categorizing the files held therein and also to a client/server architecture in an image retrieval system for content-based searching for relevant files in a particular format and having a particular file structure. The parsed files stored in a data archive managed by the document management system are subjected to a feature extraction algorithm. The features obtained are then used for producing a binary-coded inverted index which includes elements of at least two attributes and holds context information which is held in these files and is needed for content-based image retrieval. If new files or files with an extended or modified content are stored in the data archive, then it involves a parsing algorithm and also an algorithm for automatically extracting features of these files being executed under event control during every storage process, in order to extend the inverted index by individual attributes or in order to update particular elements of already existing index attributes.

18 Claims, 5 Drawing Sheets

OTHER PUBLICATIONS

B. Lutes: "Study on non-textbased information retrieval—state of the art", EU, ELPUB 106 study, 1996.

C.C.Venters, M.Cooper: "A review of content-based image retrieval systems", Technical report jtap-054, University of Manchester, 2000.

J. Ashley et al.: "Automatic and semi-automatic methods for image annotation and retrieval in QBIC", Proc. of storage and retrieval for image and video databases III, 1995, pp. 24-35.

C. Nastar et al.: "Surfimage: a flexible contant-based Image retrieval system", Proc. of ACM Multimedia, 1918, pp. 339-344.

J.R.Smith, S.-F. Chang: "VisualSEEK: a fully automated content-based image query system", Proc. of ACM Multimedia, 1996, pp. 87-98.

National Electrical Manufacturers Association: "Digital Imaging and Communications in Medicine (DICOM)—Part 3: Information Object Definitions", PS 3.3—2003, Rosslyn, Virginia, USA, 2003.

Liora Alschuler et al.: "HL7, Version 3 Standard: Clinical Document Architecture Framework", Release 1.0, 2000, pp. 1-103.

V. Christophides, S. Abiteboul, S. Cluet, M. Scholl: "From structured documents to Novel Query Facilities", SIGMOD Record, 23(2): 313-324, Jun. 1994, pp. 1-19.

W3C, S.Boag et al.: <<XQuery 1.0: An XML Query Language>>., W3C Working Draft May 2, 2003.

J. Clark, S. DeRose: <<XML Path Language (XPath) Version 1.0>>., W3C Recommandation Nov. 16, 1999.

D. Hollingsworth: "Workflow Management Coalition: The Workflow Reference Model", Hampshire 1995, pp. 1-55.

XMedia Communication System: An XML driven medical image processing and archiving environment (G.C. Sakellaris, D.I. Fotiadis) 2005Q21048.

German Office Action Issued on Oct. 25, 2005.

Le Bocez, Christel, Zapletal, Eric: "Towards content-based image retrieval in a HIS-integrated PACS", 2000, American Medical Informatics Association (AMIA). Im Internet: http://www.medicine.ucsd.edu/f2000/E001440.htm, Session S49.

Lehmann, Thomas M., et al., "Content-based image retrieval in medical applications for picture archiving and communication systems", In: Proceedings of SPIE—vol. 5033, Mai 2003, S 109-117, DOI: 10.1117/12.461942.

Müller, Henning et al.: "Efficient Access Methods for Content-Based Image Retrieval With Inverted Files" In: Proceedings of SPIE—vol. 3846: "Multimedia Storage and Archiving Systems IV", Aug. 1999, S. 461-472, DOI: 10.1117/12.12.360450.

* cited by examiner

| ID No. | Term (search query) | Document (file found) |
|---|---|---|
| 1 | {Display Name, [Coding Scheme Data], [Code Relationship Data]}, [Term-associated context data] | {Document ID, [Document Structural Context]} |
| 2 | {Display Name, [Coding Scheme Data], [Code Relationship Data]}, [Term-associated context data] | {Document ID, [Document Structural Context]} |
| 3 | ... | ... |
| 4 | ... | ... |

| ID | Patient | Diagnosis | Examination method used | Medication/Therapy | Surgical intervention | Image | Document |
|---|---|---|---|---|---|---|---|
| ... | ... | ... | ... | ... | ... | ... | ... |
| 17 | Meier, A. | Crohn's disease | MRT, ileo coloscopy, biopsy | Steroid treatment (cortisone therapy) | None | Terminal ileum, anastomotic stenosis | TI_AnaSt5.doc |
| 18 | Müller, B. | Ulcerative colitis | Sonography, MRT, oesophago-gastro-duodenoscopy, ileo coloscopy, biopsy | Steroid treatment (cortisone therapy) | None | Colon, chronic, recurrent ulcerative colitis | CO_Cucr16.doc |
| ... | ... | ... | ... | ... | ... | ... | ... |

FIG 2B 200b [2)]

| Image | Document | ID | Patient | Diagnosis | Examination method used | Medication/Therapy | Surgical intervention |
|---|---|---|---|---|---|---|---|
| ... | ... | ... | ... | ... | ... | ... | ... |
| Colon, chronic, recurrent ulcerative colitis | CO_Cucr16.doc | 18 | Müller, B. | Ulcerative colitis | Sonography, MRT, oesophago-gastro-duodenoscopy, ileo coloscopy, biopsy | Steroid treatment (cortisone therapy) | None |
| Terminal ileum, anastomotic stenosis | TI_AnaSt5.doc | 17 | Meier, A. | Crohn's disease | MRT, ileo coloscopy, biopsy | Steroid treatment (cortisone therapy) | None |
| ... | ... | ... | ... | ... | ... | ... | ... |

1) Noninverted index: primary key = "ID" [or "patient"],
   Secondary key ∈ {"Diagnosis", "Examination method used", "Medication/Therapy", "Image", "Surgical intervention", "Document"}

2) Inverted index: primary key ∈ {"Diagnosis", "Examination method used", "Medication/Therapy", "Image", "Surgical intervention", "Document"},
   Secondary key = "ID" [or "Patient"]

FIG 4

| ID No. | Clinical problem (search query) | Process definition (process model) |
|---|---|---|
| 1 | {Display Name, [Coding Scheme Data], [Code Relationship Data]} | {Process ID, [Process Definition Data]} |
| 2 | {Display Name, [Coding Scheme Data], [Code Relationship Data]} | {Process ID, [Process Definition Data]} |
| 3 | ... | ... |
| 4 | ... | ... |

400

AUTOMATIC INDEXING OF DIGITAL IMAGE ARCHIVES FOR CONTENT-BASED, CONTEXT-SENSITIVE SEARCHING The present application hereby claims priority under 35 U.S.C. §119 on German patent application number DE 103 33 530.7 filed Jul. 23, 2003, the entire contents of which are hereby incorporated herein by reference.

FIELD OF THE INVENTION

The present invention generally relates to a method for indexing data archives and also to a document management system which is suitable for content-based image retrieval. For example, it may relate to a medical document management system which permits a context-sensitive search for relevant files in a particular format and also for image and data objects referenced by these files.

To understand the inventive solution, the text below briefly discusses conventional text and image retrieval systems and also the feature extraction and pattern recognition methods based on the prior art which are necessary for content-based image retrieval.

BACKGROUND OF THE INVENTION

In the case of full text indexing known from the field of Internet search engines, the whole text of the web pages held on various web servers is indexed automatically (such as at AltaVista, HotBot or Infoseek). The relevant information is provided by "robots" or "spiders", i.e. programs which work independently to "track down" resources on the Internet by following references (hyperlinks) from already known documents.

Each new document found by such a robot is automatically "headlined" in a respective search engine's database. The way in which this takes place is dependent on the respective robot: some index the HTML title or the first paragraphs in a document, while others sift through the entire document and index each individual word letter by letter. In this context, most search engines do not store the collected documents as a full copy, since this requires a gigantic computational and storage involvement which currently only AltaVista tackles. Normally, searching is performed by creating an index table which portrays the words held on a web page in a yes/no structure.

If a search service based on full text indexing is used to search for an arbitrary term, the search engine points to all of the documents which it has searched and which contain the search term. The result which the search service immediately outputs is the URLs of the documents found in the form of hyperlinks. As such, the document found can immediately be looked up and viewed.

Depending on the search term, the search engine may not report just one hit, but rather several thousand hits. To simplify selection from a plurality of hits, most full-text based search engines automatically weight the search results, which is known as "ranking". In this context, the search engine weights the results on the basis of a mathematical method which, inter alia, evaluates the relative frequency of a search term in the documents found. The search result shows the list of hits for many search services with a percentage weighting, the documents with the highest numbers of hits being shown at the beginning of the list.

A method for producing inverted indices for indexing full-text documents is described in the article "A survey of information retrieval and filtering methods" (technical report, information filtering project, University of Maryland, College Park, Md., 1996) by C. Faloutsos and D. Oard. In this case, a distinction is drawn between indexing by a human user, semiautomatic methods and fully automatic methods. In documents which are not structured or are only slightly structured, the main difficulty with automatic indexing methods is recognition of the keywords and their context and also the exclusion of nonrelevant search terms (e.g. articles, pronouns, prepositions, conjunctions, interjections etc.).

In alternative methods based, by way of example, on a vector model for grouping similar documents (clustering), the same basic problems apply. In all cases, nonrelevant search terms are removed by using "stop word lists" ("negative dictionaries"). Further problems in the automatic production of inverted indices for full-text documents are the recognition of synonyms and of the context in which a search term, including two or more search terms, arises and also the attribution of declined nouns or adjectives and conjugated verbs to common word stems.

Conventional text-based image retrieval methods used for retrieving binary-coded image files are normally based on a simple full text search using suitable search terms. For this purpose, the content of these image files is described by a generally small set of keywords which are stored in an annotation file. In this case, the main drawback of this procedure is the reduction of complex image content to a few terms which are often able to portray the content of the image only unsatisfactorily. Thus, by way of example, the opportunities for linguistic expression for the purpose of precise verbal description of patterns, topologies, surface structures etc. are extremely limited.

For this reason, content-based image retrieval methods are necessary which automatically extract the fundamental features of an image and use them as a descriptive basis for content-based searching for images which are stored in a digital image archive. Such methods may be used in numerous fields, e.g. in medical diagnosis when comparing extracted parameters for x-ray images taken from a patient with stored image parameters for images of pathological tissue structures from an image database, in the field of remote satellite sensing for the purpose of assessing the effects of a pest attack on the forests in a region or in crime prevention for identifying perpetrators, e.g. by comparing electronically stored fingerprints with the fingerprints of a suspect which have been taken from a crime scene or by comparing the pictures from a surveillance camera with the faces stored in an electronic image archive for police criminal records.

These image databases manage large collections of images and allow searching for a number of images which are similar to a reference image or satisfy user-defined conditions. The main objective in this context is to reduce the quantity of results to a small number of suitable images which are then visualized by the user.

An overview of the image retrieval systems which exist today is given in the article "Study on non-text-based information retrieval—state of the art" (EU, ELPUB 106 study, 1996) by B. Lutes inter alia and also in the article "A review of content-based image retrieval systems" (Technical report jtap-054, University of Manchester, 2000) by C. C. Venters and M. Cooper. A few known image retrieval systems which are currently still at the research stage are the QBIC, Surfimage and Visualseek systems described in the articles "Automatic and semi-automatic methods for image annotation and retrieval in QBIC" (Proc. of storage and retrieval for image and video databases III, pp. 24-35, 1995) by J. Ashley et al., "Surfimage: a flexible content-based image retrieval system" (Proc. of ACM Multimedia, 1998, pp. 339-344) by C. Nastar et al. and "VisualSEEK: a fully automated content-based image query system" (Proc. of ACM Multimedia, 1996, pp. 87-98) by J. R. Smith and S.-F. Chang.

Conventional image description and retrieval methods are normally associated with a high level of involvement and are often unsatisfactory for adequate content description. For this reason, image databases today are expected to have the capability of content-based image retrieval. In this context, the standard approach for retrieval is based on automatic extraction and comparison of previously defined features which can be derived directly from the raw data. In particular, these highlight properties of the image content, such as dominant colors and their distribution, important shapes and textures or the global image layout. They can be weighted and can be combined with one another in different ways. Thus, it is possible to achieve an intermediate representation of the image data at a higher abstraction level. In this case, the image retrieval systems developed during research differ in terms of the methodical approach pursued in each case:

- The color-based approach involves the images to be indexed being divided into individual search spaces. The similarity of the colors identified in these search spaces is compared with the colors defined in a search query. These also include the content-based retrieval of segmented images which involves images divided into individual segments being examined according to their color distributions in the respective segments. In this context a grid including squares of selectable size is placed over an image. A color histogram is then used to determine the predominant color for each grid element, and the square in question is completely filled with this color. If a plurality of grid elements in the same color are situated next to one another, this area is combined. The information regarding the image positions of individual color areas, their color and size is then stored in an annotation file.
- Texture analysis involves division into individual image objects. In this context, the homogeneity and contrast level of an image are also measured. Using the grid split, not only the colors but also the significant features of the grid elements (e.g. contrast, two-dimensional nature, directionality etc.), which are likewise used for indexing an image, are stored as values in an annotation file.
- The edge-based approach involves evaluation of the light/dark transitions in an image, which normally arise wherever objects adjoin one another. In order to depict these contours, it is first necessary to calculate all of the edge points using an edge detector. Once all of the edge points have been located, they are combined into closed contours. These are then matched to prescribable basic geometrical shapes (e.g. triangles, squares, circles, ellipses etc.). The information obtained in this manner is then stored in the annotation file.

The similarity between a query image Bi and a number J of reference images $B_j$ (for $1 \leq j \leq J$) stored in a digital image archive is ascertained using a pattern recognition algorithm. It corresponds to a suitably defined interval dimension $d_{ij}$ for the interval between the image parameters, which are in the form of an N-dimensional feature vector $\underline{x}_i$ and have been extracted from the query image $B_i$, with the image parameters which are in the form of N-dimensional reference vectors $\underline{m}_j$ and have been extracted from the stored reference images $B_j$. This interval is normally calculated using a "similarity function". This is normally a modification of the known Minkowski interval metric—a generalization of the quadratic Euclidian interval $\|\Delta \underline{x}_{ij}\|_2^2$ between the respective feature vector xi and the individual reference vectors $\underline{m}_j$ in an N-dimensional feature space:

$$d_{ij}^2 := d^2(\underline{x}_i, \underline{m}_j) = \|\Delta x_{ij}\|_2^2 = \Delta x_{ij}^T \Delta x_{ij} = \sum_{n=0}^{N-1} \Delta x_{ij,n}^2 \ \forall \ j \text{ where} \quad (1a)$$

$$\Delta \underline{x}_{ij} := \underline{x}_i - \underline{m}_j \in \mathbb{R}^N. \quad (1b)$$

In this case, a reference vector $\underline{m}_j$ is frequently obtained by averaging the Mj stored feature vectors xqj in a class j obtained through cluster formation which are close to one another in the feature space:

$$\underline{m}_j := \frac{1}{M_j} \cdot \sum_{q=1}^{M_j} \underline{x}_{qj}. \quad (2)$$

The result of the above method is a sorted list containing J quadratic Euclidian intervals. In this case, the subscript index j for the first elements in this list refers to the reference images Bj from the image archive which are most similar to the respective query image Bi and which can then be presented to a user as hits.

In this case, the decision regarding the class to which a feature vector xi belongs is made using a minimum interval classifier which assigns the respective feature vector xi to a particular class k. For J classes with the reference vectors $\underline{m}_j$ (for $1 \leq j \leq J$), J interval metrics $d^2_{ij}$ then need to evaluated in line with the following decision rule:

$$\underline{x}_i \in \text{class } k, \quad (3)$$

$$\text{when } d_{ik}^2 = \min_j(d_{ij}^2) \text{ i.e. } d^2(\underline{x}_i, \underline{m}_k) < d^2(\underline{x}_i, \underline{m}_j) \ \forall \ j, \ j \neq k.$$

Since the features are actually extracted when the images are stored in the database, this method can be used to attain relatively short response times. During the execution time, it is thus now necessary to calculate only the interval metrics, so that the overall time required for image retrieval is significantly shortened. In addition, the method can easily be integrated into conventional database systems.

One drawback, however, is that most of the features extracted from the individual image files are highly abstract and thus cannot be used by users without specialist knowledge. Since conventional static feature extraction algorithms normally deliver a large quantity of irrelevant information which is not needed for automatic pattern comparison, methods based on dynamic feature extraction are being increasingly used today for object searching, that is to say for producing search queries in the form "Find all images $B_j \in \beta$ with the marked object X from the set $\beta := \{B_j | 1 \leq j \leq J\}$ of images stored in a digital image database", e.g. dynamic object searching using wavelet transformation.

In this context, the user selects a particular image region, which is subsequently analyzed and described by various features. This representation is then "shifted" over all of the reference images stored in an image archive and is compared with the image portions underneath. The other image regions and the object background are ignored, which means that the search can concentrate on the respective image region selected.

Since an exemplary embodiment of the present invention is based on the method for automatically indexing multimedia data archives which is preferably intended to be used in the field of medical text and image retrieval, the text below gives a short presentation of two of the main communication standards used today for describing, storing, transferring and interpreting medical image data and hence linked context information—DICOM SR ("Digital Imaging and Communication in Medicine—Structured Reporting") and HL7 ("Health Level Seven").

The communication standard DICOM, whose third part is described in detail in the specialist article "Digital imaging and communications in medicine (DICOM)" (PS 3.3-2003, Rosslyn, Va.), is a standard for interchanging and managing medical image data and other related data which has been developed in the field of radiology and will also be supported as a standard in all other medical specialist fields in future.

A DICOM document includes two subregions: header data including the "Report title", comprising DICOM code, and the "Document Content Sequence", which contains a medical data part which is coded on the basis of the SNOMED (Systemized Nomenclature for Medicine) standard. SNOMED is a description language with a thesaurus including more than 50 000 terms, the description language being used to code, index and retrieve data in patient records. The coding schemes used in this context include mnemonic, hierarchic, group-sequential, incremental and combination codes. Besides SNOMED, the DICOM standard uses numerous other coding schemes (e.g. ICD and LOINC).

The HL7 CDA standard, described in detail in specialist article "HL7 Clinical Document Architecture Framework" (Release 1.0, 2000), is an international communication standard for interchanging, managing and integrating data which are required for patient treatment.

As compared with unstructured full text documents, HL CDA and DICOM SR documents are distinguished by an explicitly coded document structure which is characterized, for example, by coded chapter and section names. In this context, for each data element for which an entry is provided, the context information associated with this data element can be read from a library file. This context information is not retained in conventional methods for indexing full text documents, which reduces the accuracy of the search process. As a result, conventional indexing provides no possible way of ensuring that a search query is supplying all of the documents relevant to a particular search query.

Structured objects stored in the DICOM SR or HL7 CDA format do not themselves contain any image objects (including header data and binary-coded image data), but rather "Unique Identifiers" (UIDs) which are used to reference image data and other objects (such as biosignal data). By way of example, DICOM SR uses UIDs which are used to denote the type and the instance of referenced objects. Within the document, these UIDs are in the context of further descriptive data, e.g. codes, which are used to denote an examination method more closely. These meta data can be used to describe the "content" of a particular referenced object and also observations in this regard.

For structured SGML documents and object-oriented databases, extensions to the query language are known, as explained in the article "From Structured Documents to Novel Query Facilities", (SIGMOD RECORD, 23(2): 313-324, June 1994) by V. Christophides, S. Abiteboul, S. Cluet and M. Scholl. For XML documents, there is the query language XQuery described in "XQuery 1.0: An XML Query Language" (W3C Working Draft 2002), this query language being suitable for information retrieval applications and using the language XPath, described in the specification "XML Path Language (XPath) version 1.0" (W3C Recommendation 1999), for addressing portions of an XML document. XPath is able to select document nodes by indicating various criteria and to implement fundamental manipulations on character strings, Boolean values and node sets and contains a simple function library which can be extended by user-defined functions. Without producing a suitable inverted index, however, these queries are limited to individual structured documents, and the search for relevant documents is inefficient.

SUMMARY OF THE INVENTION

One of the fundamental problems with conventional workflow-based document management systems used for access and flow controllers is how relevant information is supplied to a user within the context of a current process step. Of general interest in this context is the execution of process steps which, as described in the specialist article "Workflow Management Coalition: The Workflow Reference Model" (Hampshire 1995), are made available in the form of "process definitions", for example. The problem of how the system is able to support a user's decision process for selecting the information which is relevant to the respective case is not answered by this means. Instead, the user is forced to search for the information relevant to his purposes, which is in the form of the text files found by a search engine and image files referenced by these text files, for example, by viewing these files.

An embodiment of the present invention includes an object of providing an indexing method for content-based image and document retrieval which permits context-sensitive searching for relevant files in a particular format and having a particular file structure and also for image files referenced by these files. Another object of an embodiment of the invention is to provide an information management system which supports the user's decision finding when selecting the information relevant to him on the basis of analyzed document contents.

An embodiment of the invention achieves this object. Advantageous exemplary embodiments developing the concept of the invention are also defined.

In line with the object defined in the preceding section, an embodiment of the underlying invention discloses a method for automatically indexing data archives and categorizing the files held therein and also a client/server system in an image and document retrieval system for content-based searching for relevant files in at least one particular format and having at least one particular file structure and also for image files which are possibly referenced by these files and are stored in a digital image database. In this context, the server in this image retrieval system has access to a document management system which allows context-sensitive searching for relevant documents (e.g. documents containing relevant clinical and administrative patient data) and also for image and/or data objects (e.g. MRT, CT or ECG data for an individual patient or for a group of patients) which are referenced by these documents.

In this case, the basis of an embodiment of the inventive method is to use the information provided in structured documents (e.g. codes for particular indicated diagnoses, medical specialist terms etc.) for producing an inverted index in a manner which affords significant advantages over the indexing of unstructured full text documents. On this basis, the first step performed is direct retrieval of relevant documents. Next, the relevant documents are parsed and, by way of example, indicated diagnoses, clinical problems, tentative diagnoses and examination results, which are stored in appropriate document containers, are analyzed.

Normally, particular indicated diagnoses and clinical problems make one particular further course of action appropriate in the diagnostic process. By providing relevant information and displaying the measures which are suitable for solving the respective problems (e.g. in the form of a list of indicated examination methods for a particular diagnosis or of other suitable process definitions), direct planning of the work steps to be performed by the user in a particular situation (e.g. selection of a suitable examination method, of a suitable therapeutic method and/or of the administrable medicaments by the treating specialist for a patient when there is a particular tentative diagnosis) is made possible. The user is thus provided with a suitable selection of process descriptions for the further course of action.

The files) which are stored in a data archive managed by the document management system and are parsed on the basis of the rules of underlying context-free grammar are subjected to automatic feature extraction in this situation. The features obtained are then used to produce a binary-coded inverted index which includes elements of at least two attributes and holds context information which is held in these files and is needed for content-based image retrieval. When new files or files with an extended or modified content are stored in the data archive, an embodiment of the invention involves the execution of a parsing algorithm and also of an algorithm for automatically extracting features of these files under event control during every storage process, in order to extend the inverted index by individual attributes or in order to update particular elements of already existing index attributes.

Producing such a binary-coded, context-sensitive inverted index on the basis of files in a specific format (e.g. DICOM SR or HL7 CDA) allows direct provision of relevant information. One fundamental advantage of this index is that the context information provided in the files is retained, and is available for queries relating to relevant documents, when the feature extraction is performed.

In this connection, a distinction needs to be drawn between structure context and observation context, in particular. The structure context relates to the document structure, e.g. the sections in a document, which are normally denoted by a code (e.g. "diagnoses" or "to be clarified further"). Thus, by way of example, the significance of the term "pneumonia" is dependent on the structure context. Besides the structure context, the "term-associated", contents context or observation context is significant, e.g. the type of examination method used to confirm a tentative diagnosis, since various methods of diagnosis have different sensitivities and specificities. By way of example, one and the same diagnosis (e.g. "pneumonia") within the context of other clinical pictures which have been diagnosed after further examination methods have been carried out may sometimes imply different methods of therapy and medications.

By taking into account the aforementioned context information, the precision of the image and document retrieval method used for searching for relevant documents is significantly improved and direct content-based searching over the entire stock of documents is made possible. Since the images are referenced in the DICOM SR or HL7 CDA document files, the precision of document retrieval is in the foreground in this context. A "context-sensitive" index can be used to search with arbitrary precision for terms which have been obtained using a feature extraction algorithm from the contents of the files stored in the data archive and from the image files which are referenced by these files and are stored in the image database. In contrast to the restriction to querying document types (e.g. DICOM Report Title and Templates), it is therefore possible to use arbitrary contents (features extracted from text and image files) for searching. The binary-coded index uses, inter alia, the coded terms which are contained in the structured files and are defined by known coding and classification schemes (e.g. SNOMED, ICD, LOINC).

One advantage is the provision of a standard term base using the concept definitions stipulated in coding and classification schemes. By analyzing the query context and the relevant files found using the index, direct planning of the measures to be performed in individual cases is possible (e.g. selection of indicated examination methods, therapeutic methods and/or medications for a particular diagnosis).

BRIEF DESCRIPTION OF THE DRAWINGS

Further properties, features, advantages and applications of the underlying invention can be found in the subordinate dependent patent claims and also in the description below of two exemplary embodiments of the invention, which are depicted in the following drawings, in which:

FIG. 2a shows details of a binary-coded, non-inverted index for content-based searching for image files in a digital image database, which index is associated with a patient group and contains details about the period for recording clinical patient data, FIG. 2b shows details of a binary-coded, inverted index for content-based searching for image files in a digital image database, said index having been formed from the non-inverted index.

DETAILED DESCRIPTION OF THE PREFERRED EMBODIMENTS OF THE INVENTION

Figure 1:
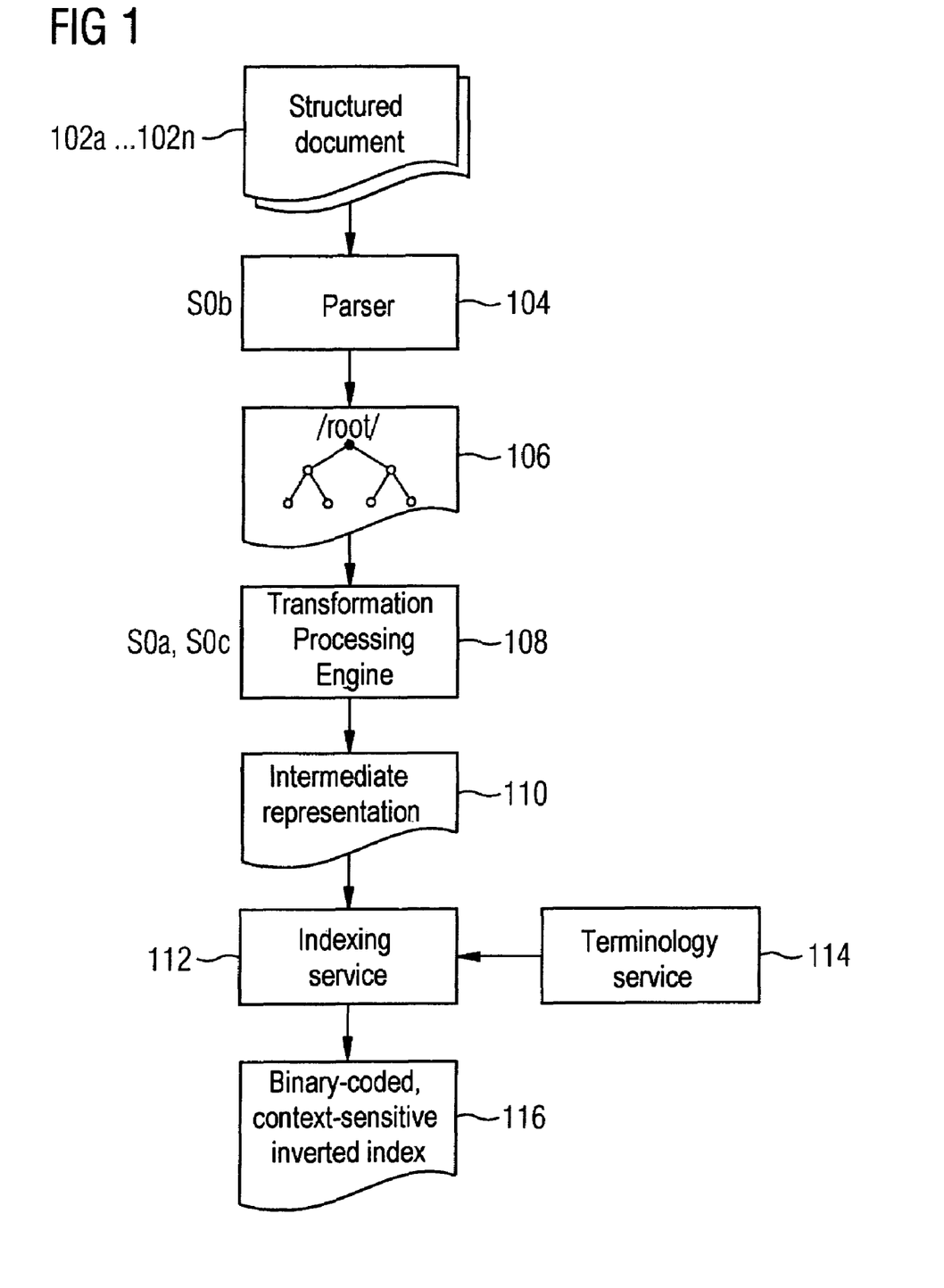
FIG. 1 shows a flowchart to illustrate the inventive method for producing a binary-coded, context-sensitive inverted index which is suitable for content-based image retrieval in a digital image database.
Figure 2:
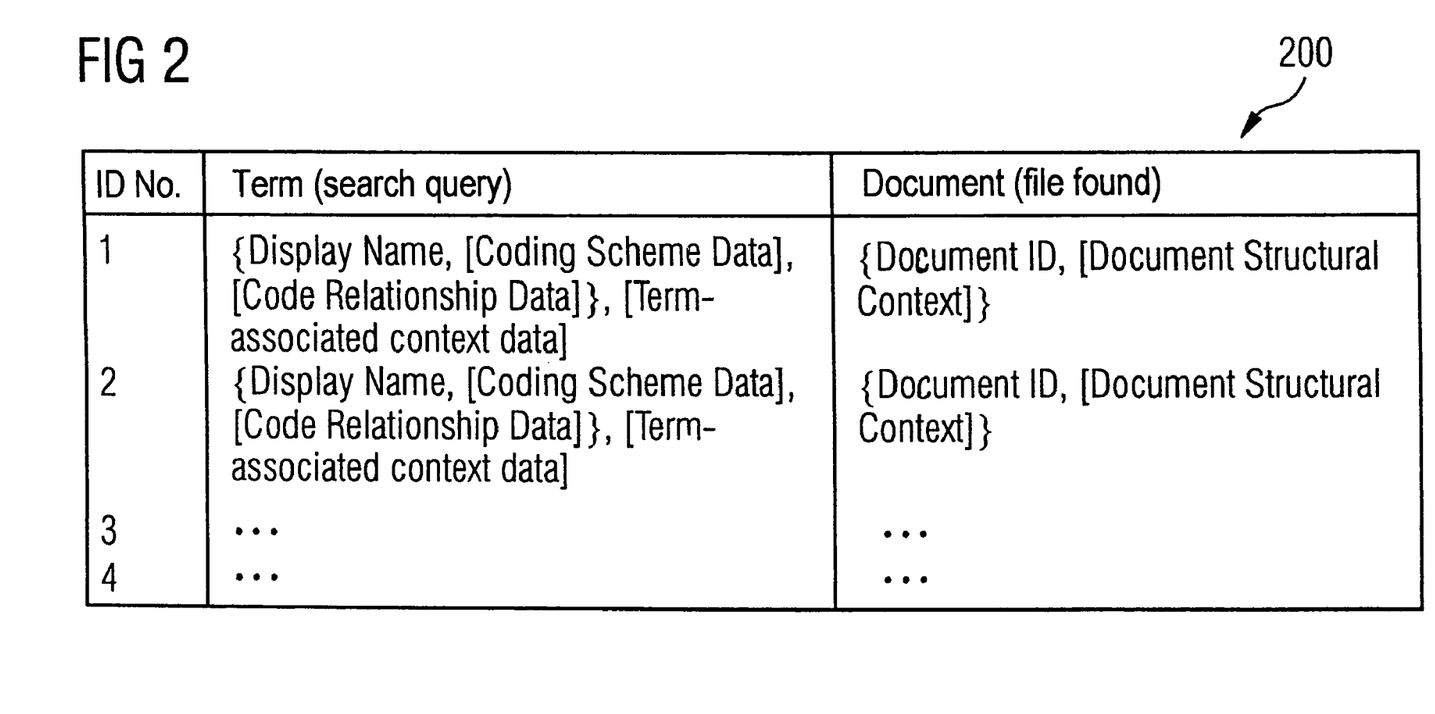
FIG. 2 shows the data structure of the structured document context, including the patient identification numbers, data relating to individual terms and their contents context and also the respective document identification numbers and structured document context data, for the purpose of assigning a binary-coded, context-sensitive inverted index to a patient group.
Figure 3:
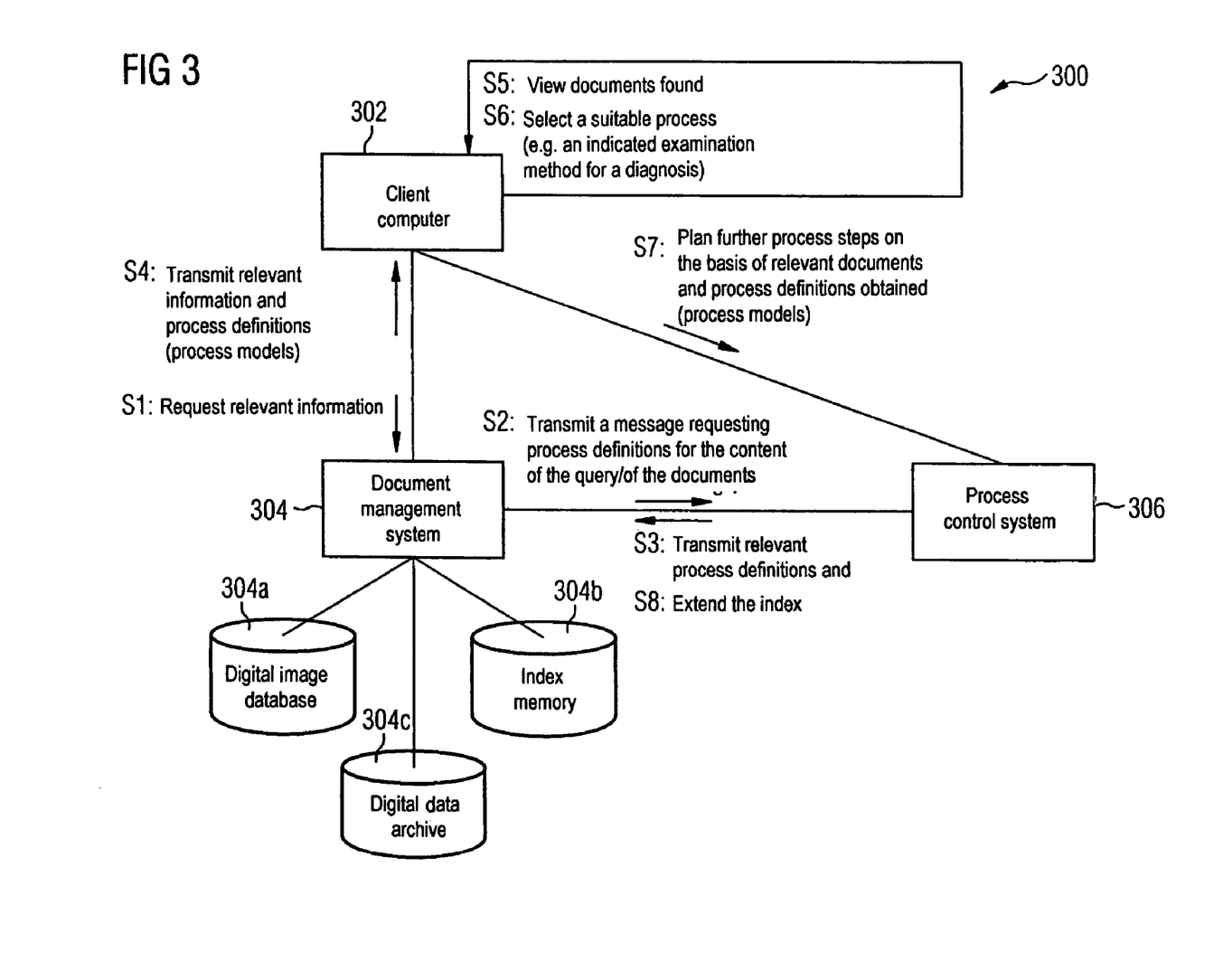
FIG. 3 shows a block diagram of the client/server architecture in an image retrieval system based on an exemplary embodiment of the present invention for content-based searching for image data in a digital image database in which image data in at least one specific format and having at least one particular file structure can be accessed using a binary-coded, context-sensitive inverted index.
Figure 4:
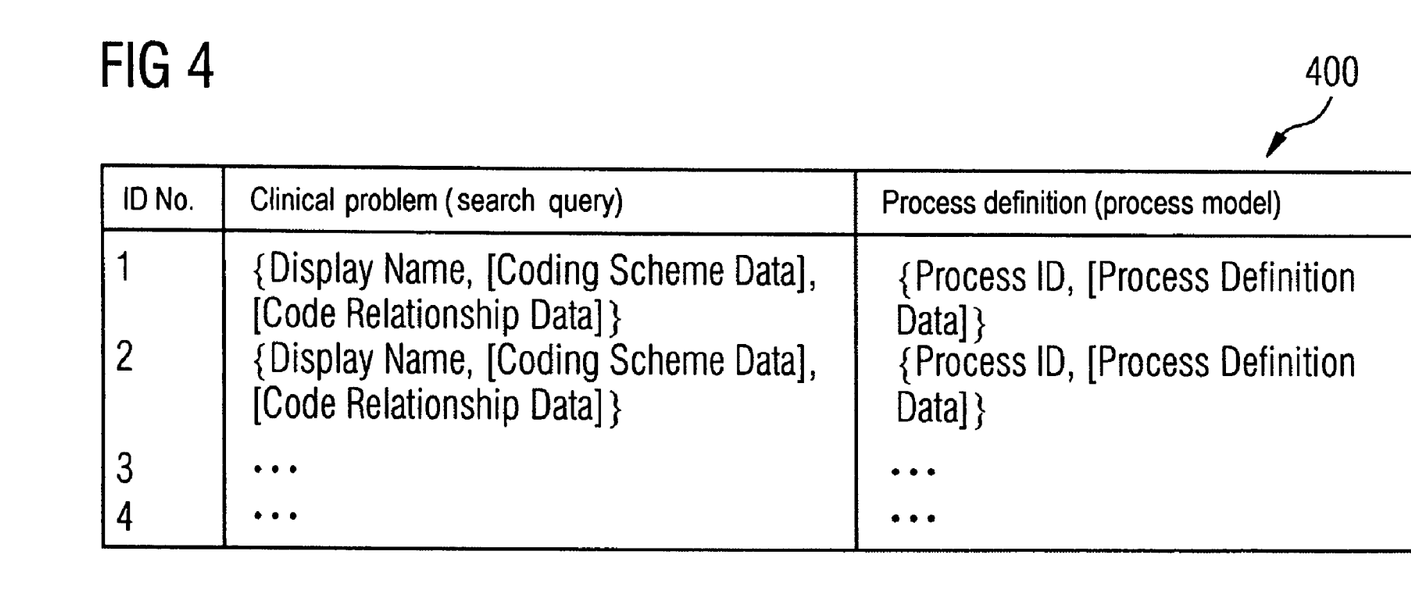
FIG. 4 shows the data structure which is used by the inventive process control system and assigns suitable measures—called process definitions—to unresolved clinical problems in the form of a list in the event of a particular diagnosis from indicated methods of examination.

The text below gives a more detailed description of the steps in an embodiment of the inventive method and of the functions of the system components contained in an exemplary embodiment of the underlying invention, as depicted in FIGS. 1 and 3. The meaning of the symbols provided with reference numerals in FIGS. 1 to 4 can be taken from the appended list of reference numerals.

A first exemplary embodiment of the present invention relates to the method illustrated in FIGS. 1 and 3 for automatically indexing multimedia data archives 304c and categorizing the files 102a-n stored therein. This method allows a content-based search for relevant files 102i in at least one particular format and having at least one particular file structure and also for image files (B1, ..., BN) which are referenced by these files and are stored in a digital image database 304a.

When a user sends a query (S1) to the document management system 304 for the purpose of searching for relevant documents 102i using the inverted index 116 by inputting search terms using a browser running on his client computer 302, a message is first transmitted (S2) from the document management system 304 to a control unit 306. In line with an embodiment of the invention, this message is used by the control unit 306 to request suitable process steps for further handling of the information contained in files 102i which have been found and are relevant to the search terms which have been input, and to forward (S3) them to the document management system 304, which provides (S4) the files 102i found and also the ascertained process steps for the user's client computer 302.

When the files 102i provided by the document management system 304 and also the image files (B1, ..., BN) referenced by these files have been looked through (S5) and at least one process step which is suitable in consideration of the information viewed has been selected (S6), the process steps selected and planned by the user are transmitted (S7) to a process control system 306 ("Workflow Engine") via the client computer 302 on the basis of the content of the provided documents 102i which have been viewed by the user. In order to extend (S8) the inverted index 116, an embodiment of the invention then involves transmission of the planned and/or selected process steps from the process control system 306 to the memory unit 304b, provided for storing the index 116, in the document management system 304 and entry of these process steps into the memory cells in the elements of index attributes provided therefor.

An inverted index 116 produced, extended and/or updated on the basis of the method described above can advantageously be used for content-based searching for files 102i in at least one particular format and having at least one particular file structure and also for image files (B1, ..., BN) which are referenced by these files and are stored in a digital image database 304a. Further advantages of the inventive method are the direct support for the user when planning necessary process steps, the reduction of the network load as a result of the direct retrieval of image data, and the shortening of the periods required for providing relevant information.

As shown in the flowchart 100 depicted in FIG. 1, the storage of one of the documents 102a-n in the database 304c in the document management system 304 automatically triggers syntactic analysis of the associated file ("parsing"). The result of this procedure is a parsing tree 106, whose nodes and leaves portray the syntactic structure of the file contents. The processing unit 108 (called "Transformation Processing Engine") converts the parsed file into a suitable parameterized representation ("intermediate representation) which is suitable for entry into the inverted index 116. The inverted index 116 is produced and updated by an indexing module 112 which accesses information relating to codes and coding schemes which are stored in a data store 114 and can be input using an application programming interface (API). In this case, the inverted index 116 is associated either with an individual patient or with a group of patients and contains the patient data recorded during an examination period.

In the first case, which is considered below, the index is assigned to a particular patient using the patient identification number (ID), which is part of the structured document context depicted in FIG. 2. This includes a data structure 200 containing an identification number (ID), data relating to individual search terms or to a plurality of search terms in a query, and their contents context and also the document identification number (document ID) and structural document context data. In this case, the objects contained in curly brackets may be contained either once or as many times as desired, while square brackets denote options which may either be omitted or contained just once FIG. 2a shows details of a specific example for a binary-coded, noninverted index 200a for content-based searching for image files Bk which are stored in the digital image database 304a. The index is associated with a group of patients and contains details about the period in which clinical patient data are recorded (e.g. diagnoses made by the doctor, indicated medications etc.). In this context, the index attribute "ID" (the column containing the patient identification numbers) is used as the primary key.

Details of a binary-coded, inverted index 200b which has been formed from the noninverted index 200a shown in FIG. 2a are depicted in FIG. 2b. In this case, the index attribute "image" (the column containing the image data recorded for examined patients during individual examinations) is used as the primary key. Normally, each image has just one associated examination method (e.g. abdominal MRT, cranial CT) which is used to perform the image acquisition.

A second exemplary embodiment of the present invention relates to a document management system 304 in an image retrieval system 300 for automatically indexing digital data archives 304c and categorizing the files 102a-z stored therein which is used to allow a content-based search for relevant files 102i in at least one particular format and having at least one particular file structure and also for image files (B1, ..., BN) which are referenced by these files and are stored in a digital image database 304a in binary-coded form. The document management system 304 also has a parser 104 for performing a syntax analysis of the contents of files 102a-z stored in the digital data archive 304c on the basis of the rules of an underlying context-free grammar and a processing unit 108 for the event-controlled conversion of parsed documents 106 into a suitable parameterized representation 110—called "intermediate representation". This representation contains features which are automatically extracted from the parsed files 102a-z and by these referenced image files (B1, ..., BN) and which are needed to produce a binary-coded inverted index 116 which is suitable for searching for context information contained in these files 102a-z and hence for content-based image retrieval during the search for the image files (B1, ..., BN) stored in a digital image database 304a. The document management system 304 also has a data store 114 or an application programming interface for providing information which is associated with codes and coding schemes and which is needed for binary coding the inverted index 116 which is to be created, and also an indexing module 112 which accesses the information on stored or input codes and coding schemes which is stored in the data store 114 and automatically indexes the intermediate representations 110 obtained for content-based image retrieval.

A third exemplary embodiment of the present invention relates to a client/server architecture in an image retrieval system 300 for content-based searching for image files (B1, ..., BN) which are stored in a digital image database 304a. In line with the invention, this client/server architecture comprises a document management system 304 which analyzes a search query from a user, which has been input using a client computer 302, for relevant information and searches a binary-coded inverted index 116 stored in a memory unit 304b for relevant documents 102i. In this case, the document management system 304 has a memory unit 304b for storing a binary-coded, context-sensitive inverted index 116 which can be used to access image files (B1, . . . , BN) in at least one particular format and having at least one particular file structure. A process control system 306 is used for event-controlled monitoring of heterogeneous processes which are initiated by the client computer 302 and by the document management system 304, for stipulating the dependencies and logic sequences in the processes and also for storing this information in the document management system 304. In line with the invention, this process control system 306 is a knowledge-based expert system, including a knowledge database and an inference system which takes collected medical specialist knowledge and stored analytical rules which have been stipulated by experts in the respective medical specialist field as a basis for weighing the information input by a doctor against these facts and rules using artificial intelligence methods, in order to derive inferences (conclusions) and to solve complex problems of a particular type in this specialist field.

As FIG. 3 shows, a user (normally a patient's treating specialist) uses his client computer 302 to send a search query for relevant information to the document management system 304, e.g. by transmitting patient data, examination records, tentative diagnoses and/or unresolved clinical problems (S1). The document management system 304 analyzes the query and searches the context-sensitive inverted index 116 held in a memory unit 304b for relevant documents 102i. On the basis of the query in conjunction with the patient data and the information contained therein, a message is sent to the process control system 306 (S2), which requests the suitable measures to be performed by the doctor in a respective situation (e.g. objectively indicated examination methods, therapeutic methods and/or medications for a particular tentative diagnosis) from the document management system 304. To this end, the process control system 306 uses the data structure 400 depicted in FIG. 4, in which unresolved clinical problems are assigned suitable medical measures in the form of a list of "process definitions".

When the document management system 304 has received these data (S3), it transmits (S4) the relevant process steps to the client computer 302 associated with the specialist in question. This specialist saves (S5) the relevant documents 102i and the image files (B1, . . . , BN) referenced by them using a browser program running on his client computer 302. In a further step (S6), he/she selects from the list of available process steps those measures which are suitable for the further course of action, so that direct planning of the measures objectively indicated in a particular situation (e.g. selection of a suitable examination method in the event of a particular tentative diagnosis) is made possible.

Any of the aforementioned methods may be embodied in the form of a program. The program may be stored on a computer readable media and is adapted to perform any one of the aforementioned methods when run on a computer. Thus, the storage medium or computer readable medium, is adapted to store information and is adapted to interact with a data processing facility or computer to perform the method of any of the above mentioned embodiments.

The storage medium may be a built-in medium installed inside a computer main body or removable medium arranged so that it can be separated from the computer main body. Examples of the built-in medium include, but are not limited to, rewriteable involatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable involatile memory, such as memory cards; and media with a built-in ROM, such as ROM cassettes.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for allowing a content-based search of a data archive for files and for image files referenced by the files, the method comprising:

extracting information provided in structured documents from a number of files managed by a document management system in an image retrieval system, to produce an inverted index for content-based searching of image files in a digital image database, including elements of at least two attributes, including a location of files responsive to a search query and process steps to be taken based on the query results, and context information held in the files and used for content-based image retrieval;

executing a parsing algorithm and an algorithm for extracting features of at least one of new files and one of the files whose content has been at least one of extended and altered when the files are stored in the data archive managed by the document management system for the purpose of updating the inverted index;

providing a selection of process steps for further handling of information contained in files which have been found based on the inverted index;

sending a context-sensitive query to the document management system to search for documents using the inverted index by inputting context-sensitive search terms using a browser program running on a client computer;

transmitting a message from the document management system to a process control system in which the process steps for further handling of the information contained in files which have been found and axe relevant to the search terms entered are requested;

forwarding the process steps ascertained by the process control system to the document management system;

providing the files found and the process steps to the client computer;

viewing the files provided by the document management system and viewing the image files referenced by the files provided;

selecting at least one process step which is suitable in consideration of the information viewed; and transmitting at least one of selected and planned process steps, including the elements of the two attributes from the client computer to the process control system on the basis of the content of the documents provided, wherein the process steps are related to at least one of medical examinations, therapeutic treatments and medications for a diagnosis included in the inverted index.

2. The inverted index at least one of produced, extended and updated by the method as claimed in claim 1, for content-based searching for at least one of the files and image files, referenced by the files and stored in a digital image archive.

3. The method for allowing a content-based search of a data archive, as claimed in claim 1, further comprising extending the inverted index by executing a parsing algorithm and an algorithm for extracting features of at least one of new files and one of the files whose content has been at least one of extended and altered due to selection of the at least diagnostic and therapeutic process steps.

4. The method for allowing a content-based search of a data archive, as claimed in claim 1, further comprising producing the inverted index in at least one of a DICOM (Digital Imaging and Communication In Medicine) format and a HL7 (Health Level 7) format.

5. The method for allowing a content-based search of a data archive, as claimed in claim 1, further comprising associating the inverted index with one of an individual patient and a group of patients, wherein the inverted index includes patient data recorded during an examination period.

6. A document management system of an image retrieval system including a computer software product stored on a computer readable medium in which computer instructions are stored, which instructions, when executed by a computer, cause the computer to perform a content-based search of a data archive for relevant files and for image files referenced by the files, comprising:
   a parsing module configured to perform a syntax analysis of contents of files stored in the data archive; and
   a processing module configured to provide event-controlled conversion of parsed documents into a suitable intermediate representation containing features extracted from parsed files and from image files referenced by the parsed files, said features being usable to produce an inverted index for content-based searching of image files in a digital image database, including elements of at least two attributes including a location of files responsive to a search query of the data archive and process steps to be taken based on results of the search query, for context information held in the files and hence for content-based image retrieval during the search for image files in an image archive including a collected medical knowledge database and an inference system that stores collected medical knowledge and the stored analytical rules to weigh terms of the search against the collected medical knowledge and the stored analytical rules to derive inferences, the processing module being further configured to provide a selection of at least one of diagnostic and therapeutic process steps for further handling of information contained in the files based on the at least two attributes.

7. The document management system as claimed in claim 6, further comprising:
   at least one of a data storing module and an application programming interface configured to provide information associated with codes and coding schemes and usable for coding the inverted index to be created; and
   an indexing module configured to access information relating to at least one of stored and input codes and coding schemes stored in the data store and configured to perform automatic indexing of intermediate representations obtained for content-based image retrieval.

8. A client/server system in an image retrieval system for content-based searching for image files stored in an image archive including,
   a client computer configured to send a search query for relevant information, and
   a document management system, including a digital image database having elements of at least two attributes including a location of files responsive to a search query and process steps related to at least one of diagnosis and treatment of a patient to be taken based on the query results, an index memory and a digital data archive, configured to analyze the search query and search an inverted index of image files in a digital image database, stored in a memory unit and usable to access image files, and for providing a selection of process steps for further handling of information contained in files found based on the inverted index, the client/server system comprising:
   a process control system including a computer software product stored on a computer readable medium in which computer instructions are stored, which instructions, when executed by a computer, cause the computer to perform event-controlled monitoring of heterogeneous processes initiated by the client computer and the document management system, stipulating dependencies and logic sequences for the processes, and storing this information in the document management system, the process control system including a collected medical knowledge database and an inference system that stores collected medical knowledge and stored analytical rules to weigh the search query against the collected medical knowledge and the stored analytical rules to derive inferences, wherein
   the process controls system is configured to control transmitting at least one of selected and planned process steps, including the elements of the two attributes from the client computer to the process control system on the basis of the content of the documents provided.

9. The client/server system as claims in claim 8, the process steps are related to at least one of medical examinations, therapeutic treatments and medications for a diagnosis included in inverted index.

10. A document management system of an image retrieval system including a computer software product stored on a computer readable medium in which computer instructions are stored, which instructions, when executed by a computer, cause the computer to perform automatic indexing data archives and categorizing files stored therein for the purpose of allowing a content-based search for relevant files and also for image files referenced by the files and are held in an image archive, comprising:
   instructions for performing a syntax analysis of the contents of files stored in the data archive;
   instructions for event-controlled conversion of analyzed files into a suitable intermediate representation containing features extracted from the analyzed files and from the image files referenced by the analyzed files, said features being usable to produce an inverted index, including an image index attribute relating to an image recorded for an examined patient, for searching for context information held in the files and hence for content-based image retrieval during the search for image files in the image archive;
   instructions for providing a selection of process steps for further handling of information contained in the files;
   instructions for transmitting at least one of selected and planned process steps, including elements of two attributes including a location of files responsive to a search query and process steps related to at least one of diagnosis and treatment of a patient to be taken based on the query results; and
   instructions for extending the inverted index by transmitting information contained in new documents from a process control system, that includes a collected medical knowledge database and an inference system that takes collected medical knowledge and stored analytical rules to weigh the search query against the collected medical knowledge and stored analytical rules to derive inferences, to a memory unit in the document management system that stores the inverted index.

11. The document management system as claimed in claim 10, further comprising:
instructions for providing information associated with codes and coding schemes and usable for coding the inverted index to be created; and
instructions for accessing information relating to provided information associated with at least one of codes and coding schemes and for performing automatic indexing of the intermediate representations obtained for content-based image retrieval.

12. The document management system as claimed in claim 10, wherein the process steps are related to at least one of medical examinations, therapeutic treatments and medications for a diagnosis included in inverted index.

13. A client/server system in an image retrieval system including a computer software product stored on a computer readable medium in which computer instructions are stored, which instructions, when executed by a computer, cause the computer to perform content-based searching for image files stored in an image archive including,
instructions for sending a search query for relevant information in a collected medical knowledge database and an inference system that takes the collected medical knowledge and stored analytical rules to weigh the search query against the collected medical knowledge and stored analytical rules to derive inferences, and
instructions for analyzing the search query, for searching an inverted index including an image index attribute relating to an image recorded for an examined patient, stored and usable to access image files, and for providing a selection of at least one of diagnostic and therapeutic process steps for further handling of information contained in files found based on the inverted index, the client/server system comprising:
instructions for event-controlled monitoring of heterogeneous processes initiated by a means for sending and a means for analyzing, stipulating dependencies and logic sequences for the processes, and storing this information in the means for analyzing; and
instructions for transmitting at least one of the selected diagnosis and therapeutic process steps to the means for sending.

14. A method for a data archive for files and for image files referenced by the files, the method comprising:
producing an inverted index including elements of at least two attributes and context information held in the files and used for content-based image retrieval;
providing a selection of at least one of diagnostic and therapeutic process steps for further handling of information contained in files which have been found based on the inverted index;
sending a query to a document management system to search for documents using the inverted index by inputting search terms using a browser program running on a client computer;
transmitting a message from the document management system to a process control system in which process steps for further handling of the information contained in files which have been found and are relevant to the search terms entered are requested;
forwarding the process steps ascertained by the process control system to the document management system;
providing the files found and the process steps to the client computer;
viewing the files provided by the document management system and viewing the image files referenced by the files provided;
selecting at least one process step which is suitable in consideration of the information viewed; and
transmitting at least one of selected and planned process steps from the client computer to the process control system on the basis of the content of the documents provided.

15. The method as claimed in claim 14, further comprising a step of extending the inverted index by transmitting selected process steps from the process control system to a memory unit in the document management system and entering these process steps into the memory cells in the elements of index attributes is provided.

16. The inverted index at least one of produced, extended and updated by the method as claimed in claim 14, for content-based searching for at least one of the files and image files, referenced by the files and stored in a digital image archive.

17. An apparatus for a data archive for files and for image files referenced by the files, the apparatus including a computer software product stored on a computer readable medium in which computer instructions are stored, which instructions, when executed by a computer, cause the computer to perform a method of automatic indexing, the method comprising:
executing instructions for producing an inverted index for content-based searching of image files in a digital image database, including elements of at least two attributes, including a location of files responsive to a search query and process steps to be taken based on the query results, and context information held in the files and used for content-based image retrieval;
executing instructions for providing a selection of at least one of diagnostic and therapeutic process steps for further handling of information contained in files which have been found based on the inverted index; and
executing instructions for updating the inverted index, including an image index attribute relating to an image recorded for an examined patient, by executing a parsing algorithm and an algorithm for extracting features of at least one of new files and one of the files whose content has been at least one of extended and altered due to selection of the at least diagnostic and therapeutic process steps.

18. An apparatus for a data archive for files and for image files referenced by the image files, the apparatus comprising a computer software product stored on a computer readable medium in which computer instructions are stored, which instructions, when executed by a computer, cause the computer to:
execute instructions for extracting features from a number of files managed by a document management system in an image retrieval system, to produce an inverted index for content-based searching of image files in a digital image database, including elements of at least two attributes and context information held in the files and used for content-based image retrieval;
executing a parsing algorithm and an algorithm for extracting features of at least one of new files and one of the files whose content has been at least one of extended and altered when the files are stored in the data archive managed by the document management system for the purpose of updating the inverted index;
executing instructions for providing a selection of at least one of diagnostic and therapeutic process steps for further handling of information contained in files which have been found based on the inverted index;

executing instructions for sending a query to the document management system to search for documents using the inverted index by inputting search terms using a browser program running on a client computer;

executing instructions for transmitting a message from the document management system to a process control system in which the process steps for further handling of the information contained in files which have been found and are relevant to the search terms entered are requested;

executing instructions for forwarding the process steps ascertained by the process control system to the document management system;

executing instructions for providing the files found and the process steps to the client computer;

executing instructions for viewing the files provided by the document management system and viewing the image files referenced by the files provided;

executing instructions for selecting at least one process step which is suitable in consideration of the information viewed;

executing instructions for transmitting at least one of selected and planned process steps from the client computer to the process control system on the basis of the content of the documents provided, wherein the process steps are related to at least one of medical examinations, therapeutic treatments and medications for a diagnosis included in inverted index.

* * * * *